United States Patent [19]

Schreurs et al.

[11] Patent Number: 5,196,516
[45] Date of Patent: Mar. 23, 1993

[54] PSEUDORABIES VIRUS VACCINE

[75] Inventors: Christa S. Schreurs, Kerken; Thomas C. Mettenleiter, Tübingen; Artur J. Simon, Munich; Noëmi Lukacs, Düsseldorf; Hanns J. Rziha, Tübingen, all of Fed. Rep. of Germany

[73] Assignee: Akzo N.V., Arnhem, Netherlands

[21] Appl. No.: 383,833

[22] Filed: Jul. 21, 1989

[30] Foreign Application Priority Data

Aug. 1, 1988 [EP] European Pat. Off. ............ 112479.6

[51] Int. Cl.$^5$ ............................................ C07K 15/14
[52] U.S. Cl. ................................. 530/395; 530/806; 530/350; 424/89
[58] Field of Search ................ 530/350, 395; 424/89

[56] References Cited

U.S. PATENT DOCUMENTS 4,711,850 12/1987 Kio et al. ..................... 435/235

OTHER PUBLICATIONS

Robbins et al. 1987. J. Virol. 61(9):2691-2701.
Lerner, R. A. 1982. Natur. 299:592-596.
Simon et al. 1989. J. gen Virol. 70:1239-1246.
Halling, S. M. 1985. Molecular Genetics, Inc. (Meet., 54) (Dialog File 357, DBA Accession No.: 86-08964. Abstract).
Mettenleiter et al. 1986. Virology 152:66-75.
Wunner et al. 1985. Virology 140:1-12.

Primary Examiner—Margaret Moskowitz
Assistant Examiner—Keith C. Furman
Attorney, Agent, or Firm—Donna Bobrowicz; William M. Blackstone

[57] ABSTRACT

The present invention is concerned with a pseudorabies virus (PRV) vaccine comprising a polypeptide of the PRV glycoprotein gII or a fragment thereof which was shown to be the site of interaction of PRV neutralizing antibodies. Vector vaccines capable to express a polynucleotide fragment coding for such a polypeptide also form part of the present invention.

5 Claims, 7 Drawing Sheets

COMPARISON OF DNA SEQUENCE OF PHYLAXIA (WT) AND MAR-MUTANTS

| Sequence position | 652 | 660 | 677 |
|---|---|---|---|
| mIN-4 | CATCTCGTGCGACC... Cys | CTGCACCGGCAAC... | CTACGAGGACTACAA |
| m1/5 | CATCTCGCGCGACC... | CTGCACCCGCAAC... Arg | CTACGAGGACTACAA |
| m5/14 | CATCTCGCGCGACC... | CTGCACCGGCAAC... | CTACGAGTACTACAA Tyr |
| wt | CATCTCGCGCGACC... Arg | CTGCACCGGCAAC... Gly | CTACGAGGACTACAA Asp |

```
       2910      2920      2930      2940      2950      2960      2970      2980
AACTACGTGCGCATGGTGGAGGTGCCCGAGACGATCAGCACGCGGTGACCTGAACCTGACGCTGCTGGAGGACCGCGAG
AsnTyrValArgMetValGluValProGluThrIleSerThrArgValThrLeuAsnLeuThrLeuLeuGluAspArgGlu
        680                              690                              700
 2990      3000      3010      3020      3030      3040      3050      3060
TTCCTGCCCCTCGAGGTGTACACGCGCGAGAGCTCGCCGACACGGGCCTCCTGGACTACAGCGAGATCGAGCGCCGCAAC
PheLeuProLeuGluValTyrThrArgGluTyrThrArgGlyLeuAlaAspThrGlyLeuLeuAspTyrSerGluIleGlnArgArgAsn
         710                              720                              730
 3070      3080      3090      3100      3110      3120      3130      3140      3150
CAGCTGCACGCGCTCAAGTTCTACGACATGACCGCGGTGGTCAAGGTGGACCACAACGTGGTGCTGCTGCGCGGCATCGCC
GlnLeuHisAlaLeuLysPheTyrAspIleAspArgValValLysValAspHisAsnValValLeuLeuArgGlyIleAla
        740                              750
 3160      3170      3180      3190      3200      3210      3220      3230
AACTTTTCAGGGCGGACGTGGGCGACGTGGGCCGCCGACGTGGTCCTGGGCAAGGTGGTGCTGGGCGGGGCCGTGATCTCGGCC
AsnPhePheGlnGlyLeuGlyAspGlyAspValGlyAlaValGlyLysValLeuGlyValAlaThrGlyAlaValIleSerAla
760                              770                              780
 3240      3250      3260      3270      3280      3290      3300      3310
GTCGGCGGCATGGTGTCCTTCCTGCCAACCCCTTCGGGGGCGCTGCCATGGGGCTGCTGGTGCTGGCCGGCCTGGTCGCG
ValGlyGlyMetValSerPheLeuSerPheAsnProPheGlyAlaLeuAlaIleGlyLeuLeuValLeuAlaGlyLeuValAla
         790                              800                              810
 3320      3330      3340      3350      3360      3370      3380      3390
GCCTTCCTGGCCTACCGGCACATCTCGCGCCTGCGTCGCAACCCCATGAAGGCCCTGTACCCGTCACGACGAAGACGCTC
AlaPheLeuAlaTyrArgHisIleSerArgLeuArgArgAsnProMetLysAlaLeuTyrProValThrThrLysThrLeu
        820                              830                              840
 3400      3410      3420      3430      3440      3450      3460      3470
AAGGAGGAGGCCCTCGACGAGGCAGCAGGAGCACAAGGCGCGAAGAGAAGGGCGCGGCCCCGGCGCTGCTGGCCAGCCGCGTCGGGGCG
LysGluAspGlyValAspGlyValAspGlyValAspGlyValAspGlyValAspGlyValAspGlyValAsp... (skip)
         850                              860
 3480      3490      3500      3510      3520      3530      3540      3550
GTGTCGGCCCTCGAGCAGCAGGAGCACAAGGCGCGAAGAGAAGGGCGCGGCCCCGGCGCTGCTGGCCAGCCGCGTCGGGGCG
ValSerAlaLeuGluGlnGlnGluHisLysAlaArgLysLysAsnSerGlyProAlaLeuLeuAlaSerArgValGlyAla
        870                              880                              890
 3560      3570      3580      3590      3600      3610      3620      3630
ATGGCCACGCGCGCCGGACTACCAGCGCCTCGAGAGCGGAGGAGGCCCGACGCCCTGTAGCCCCGGCCCCGGGAAACAAT
MetAlaThrArgArgArgHisTyrGlnArgLeuGluSerGluAspProAspAlaLeu+++
         900                              910 913
 3640      3650      3660      3670      3680      3690      3700      3710
AAAGATGCGCTTGTTTGGCAACACGTCTCCGTCTCCGTCCCCTCTCCCTCCGTCCCCTCCCTCCGTCCCTCCCC
 3720      3730      3740      3750      3760      3770      3780      3790
CTCGTCCCCTCTCCGTCCCCTCTCCGTCCCCTCTCCGTCCCCTCTCCGTCCCCTCTCCGTCCCCTCTCCCTCCGT
 3800      3810      3820      3830      3840      3850      3860      3870
CCCTCTCCCTCCGTCCCCTCTCCGTCCCCTCTCCGTCCCCTCTCCGTCCCCTCTCCGTCCCCTCCCTCCGTCCCTCT
```

FIG. I-4

```
3880      3890      3900      3910      3920      3930      3940      3950      3960
CCCCTCCGTCCCTCTCCCCTCCGTCCCTCTCCCCTCCGTCCCTCTCCCCTCCGTCCCTCTCCCCTC
     3970      3980      3990      4000      4010      4020      4030      4040
CGTCCCTCTCCCCCCCCCCGTCCCTCTCCCCTCCGTCCCTCTCCCCTCCGTCCCTCTCCCCTCCG
4050      4060      4070      4080      4090      4100      4110      4120
TCCCTCTCCCCTCCGTCCCTCTCCCCTCCGTCCCTCTCCCCTCCGTCCCTCTCCCCTCCGTCCTC
     4130      4140      4150      4160      4170      4180      4190      4200
TCCCCCCCGTCCCTCTCCCCTCCCCCCCCGTCCCTCTCCCCTCCCCCCGTCCCTCTCCGTCCCTC
4210      4220      4230      4240      4250      4260      4270      4280
CCCTCCCGTCCCTCTCCCCTCCCCCCCCCCGTCCCTCTCCCCTCCGTCCCTCTCCCCTCCCCCCT
     4290      4300      4310      4320      4330      4340      4350      4360
CCGTCCCTCTCCCCCCGTCCCTCTCCCCTCCCCCCCCCCGTCTCCCCCCCGTCCCTCTCTCCCCTCC
4370      4380      4390      4400      4410      4420      4430      4440
GTCCCTCTCCGTCCCTCTCCCCTCCCCCCCGTCCCTCTCCCCTCTCCCCCCCGTCCCTCCGTCCCT
     4450      4460      4470      4480      4490      4500      4510      4520
CTCCCCTCCGTCCCTCTCCCCTCCCCCCTCCGTCCCCCTCCGTCCCGGACCACGATGACACGCACGC
4530      4540      4550      4560      4570      4580      4590      4600
CGTGTGTACAGAATTAGAAAAAAACTTTATTTCCACACACGGGGGCAACGGGGGAAACCATACAACGGGGGGGTCCGCGGG
     4610      4620      4630      4640      4650      4660      4670      4680
GCCGTCACACGCGCCAGCTCTTGCGCGCGAGCGCGGTGGCCGGTGAGGTCGATGATGACGGGTCGGGGGTGCTGGTACAGGC
4690      4700      4710      4720      4730      4740      4750      4760      4770
CGTCGTCCGCGGGGTCCGGGGGCGGGGGTGCTGGGTACACGTGGTCGGGCTCGCCCTGGGGGGGACCGGGGGGGGGTGGCGG
     4780      4790      4800      4810      4820      4830      4840      4850
GGGCCGGCCGAGTCGAGGGGACCCCGCCCTGCGCGGGGTCGGGGCTCGTGCGCGGAGAGCCGGCGGCGACGAAGCGCTGGG
4860      4870      4880      4890
CGGGCGGAACGAGGCCGGAACCCCGGCCGGAAGCTGGTGCGCATGC
```

FIG. 1-5

COMPARISON OF DNA SEQUENCE OF PHYLAXIA (WT) AND MAR-MUTANTS

| Sequence position | 652 | 660 | 677 |
| --- | --- | --- | --- |
| mIN-4 | CATCTCGTGCGACC...(TGC: Cys) | CTGCACCGGCAAC... | CTACGAGGACTACAA |
| ml/5 | CATCTCGCGCGACC... | CTGCACCCGCAAC...(CGC: Arg) | CTACGAGGACTACAA |
| m5/14 | CATCTCGCGCGACC... | CTGCACCGGCAAC... | CTACGAGTACTACAA (TAC: Tyr) |
| wt | CATCTCGCGCGACC...(CGC: Arg) | CTGCACCGGCAAC...(GGC: Gly) | CTACGAGGACTACAA (GAC: Asp) |

FIG. 3

PSEUDORABIES VIRUS VACCINE

The present invention is concerned with a polypeptide having immunizing activity characteristic of the glycoprotein gII of pseudorabies virus (PRV), a polynucleotide coding for such a polypeptide, a recombinant DNA and a host comprising these, as well as a vaccine for the immunization of mammals against Aujeszky's disease.

Pseudorabies virus is the causative agent of Aujeszky's disease which induces serious economic losses especially among piglets in swine breeding farms and leads to latent infection in older animals.

PRV is a member of the herpes virus group, which contains in its core a double-stranded DNA molecule with molecular weight of about $90 \times 10^6$ daltons (D), separated by inverted repeats into a long and a short unique region—$U_L$ and $U_S$, respectively. This DNA core is enclosed by an icosahedral capsid consisting of 162 capsomers. Around the capsid is found an amorphous structure called the tegument, which in turn is enclosed by the envelope with small spikes protruding from it. The envelope is acquired from the cellular membrane when the nucleocapsid buds through virus-modified patches of the cellular membrane. As a result the envelope largely consists of cellular membrane material with viral glycoproteins embedded therein. Probably these envelope glycoproteins are the only proteins exposed at the surface of intact PRV.

Five structural envelope glycoproteins of PRV whose genes are mapped and sequenced are indicated as gI, gII, gIII, gp 50 and gp 63, and have approximate molecular weights of 122, 155, 90, 50 and 63 kD, respectively (Lukàcs et al.(1985); J.Virol 53(1), 166–173; Hampl et al. (1984); J. Virol. 52 (2), 583–590). All these glycoproteins are sulphated as well, be it to varying degrees—gIII seems to be sulphated to a much higher extent than the others.

It is known that the herpes virus glycoproteins that are expressed at the surface are involved in the generation of virus neutralizing and protective antibodies. It has been shown that antibodies against gII can effectively neutralize PRV in vitro. Furthermore, after passive immunization of mice with antibodies against gII, protection against a lethal PRV infection is obtained. The glycoprotein gII is stably expressed by all PRV isolates tested so far, seems highly stable against mutation and it is believed that this protein is essential for virus replication.

It has been found, according to the present invention, that the glycoprotein gII can play an essential role in the neutralization of PRV by antibodies.

More in particular, it has been found that a specific region of gII is involved in said neutralization of PRV.

Therefore, the present invention is concerned with a polypeptide that, although it differs from the native glycoprotein gII, comprises at least one polypeptide fragment of gII, or a polypeptide having the same immunological characteristics as said polypeptide fragment.

The present invention is in particular concerned with a polypeptide fragment which for the gII glycoprotein of the PHYLAXIA strain is roughly positioned between the amino acid No.'s. 590 and 710 (FIG. 1). The corresponding fragments of the gII glycoproteins of other PRV strains form part of the present invention too.

Within the glycoprotein gII at least 4 epitopes are located which interact with distinct groups of monoclonal antibodies all capable to effectively neutralize the infectivity of PRV. These 4 groups of monoclonal antibodies are represented by the monoclonal antibodies produced by the hybridoma strains 1/5, IN4, N4 and N12, deposited with the European Collection of Animal Cell Cultures at Porton Down, U.K. under the deposit numbers 88080103, 88080102, 88080101 and 88080104, respectively. The hybridomas were all deposited on Aug. 1, 1988, at Public Health Laboratory Service Centre for Applied Microbiology and Research, Porton Down, Salisbury, Wilts. U.K., SP4 OJG.

The polypeptide fragments corresponding with these epitopes also form part of the present invention.

The above-noted polypeptides according to the present invention are useful in or as synthetic vaccines for the immunization of mammals against Aujeszky's disease.

In some cases the ability to raise neutralizing antibodies of these polypeptides per se may be low. In these instances, for effective immunization, the immunogenicity of these polypeptides should be raised. This can be established, for example, by presenting the polypeptides coupled to some carrier. Suitable carriers for this purpose are macromolecules, such as natural polymers (proteins, like key-hole limpet hemocyanin, albumin, toxins), synthetic polymers like poly-amino acids (poly-lysine, poly-alanine), or micelles of amphiphilic compounds like saponins. Alternatively the polypeptides may be provided as polymers thereof, preferably linear polymers. These linear polymers may contain multiple copies of the same polypeptide, or of two or more different polypeptides according to the invention, and optionally may contain polypeptides representing fragments of other proteins (e.g. from PRV or from another pathogen) as well. The respective relevant polypeptides may be coupled directly to each other or may be coupled by means of a linking group, preferably one or more amino acid.

Both the polypeptide-carrier-bound and the linearly polymerized polypeptides according to the invention may advantageously be prepared as coupled products using recombinant DNA (rDNA) techniques whereby a polynucleotide coding for said polypeptide is inserted into a suitable expression vector.

A further alternative for the effective presentation of the polypeptides according to the invention is the covalent coupling of these polypeptides with amphiphilic compounds having adjuvant properties. Optionally these coupling products may be associated by non-covalent bonds to form complexes like micelles.

A further type of vaccine according to the invention comprises so-called vector vaccines. In this type of vaccine a polynucleotide sequence coding for a gII polypeptide according to the invention is grafted by recombinant techniques into the genetic material of a host micro-organism (e.g. virus or bacterium) thereby enabling the latter to express the gII polypeptide within an in vitro cell system or directly in an animal to be protected against Aujeszky's disease. Suitable examples of vaccine vectors (without limiting the scope of the present invention) are for example pox viruses (such as vaccinia, cowpox, rabbit pox), herpes viruses (such as chicken pox (Varizella Zoster) virus), bacteriophages, adenoviruses, influenza viruses, or bacteria (such as *Escherichia coli* and Salmonella).

Still a further aspect of the present invention is a so-called anti-idiotype antibody to the gII polypeptide. Such an antibody is directed against the idiotype of the antibody specific for the gII polypeptide according to the invention. With the idiotype is meant that part of the antibody which is actually in direct contact with the polypeptide and which is responsible for the specific binding of that polypeptide to the antibody. Hence, the so-called variable fragment (Fv) of an anti-idiotype antibody exactly mimicks the epitope of the particular gII polypeptide. For this reason the anti-idiotype antibody for gII polypeptide or a variable fragment thereof, will upon administration to an animal give rise to antibodies against the particular gII epitope. An anti-idiotype vaccine for gII polypeptide may contain such an anti-idiotype antibody or an Fv part thereof, optionally bound to a carrier. Such an antibody may be a polyclonal antibody but more advantageously it may be a monoclonal anti-idiotype antibody or a mixture of several of these with different specificities.

The above-described vaccines are suitable for active immunization against Aujeszky's disease.

For passive immunization of animals against Aujeszky's disease use can be made of antibodies and more in particular monoclonal antibodies directed against the gII polypeptide of the invention or fragments thereof. Suitable representatives of such monoclonal antibodies against gII polypeptide are described in Example 1.

The antibodies and in particular monoclonal antibodies referred to in the description of the present invention can be prepared by methods known in the art such as immunization of an animal with gII polypeptide, immortalization of thus obtained antibody-producing cells and recombinant techniques.

Wherever throughout the present specification reference is made to recombinant techniques this refers to methods by which nucleic acids from different sources are linked to yield genetic material suited for replication and, where appropriate, for expression of the gII polypeptides according to the invention or antibodies against these.

In view of said recombinant techniques polynucleotides which code for a polypeptide according to the invention also form part of the present invention. More in particular this relates to polynucleotides coding for the entire gII polypeptide of about 121 amino acids as represented by the nucleotide base numbers about 2639 through about 3001 in FIG. 1. This also relates to subsequences thereof coding for a particular gII epitope, for chimeric polypeptides containing one or more of the gII epitopes or the entire about 121 amino acids gII polypeptide, and to polynucleotides which code for these same polypeptides making use of different codons for one or several of the respective constituting amino acids.

A vaccine according to the invention contains as its active ingredient either a gII-derived polypeptide, or an antibody against this polypeptide, or an anti-idiotype antibody for said polypeptide.

The vaccine with the gII-derived polypeptide or the anti-idiotype antibody therefore generally can be administered in a conventional active immunization scheme: single or repeated administration optionally preceded by or followed by an administration of inactivated PRV. The administration of the vaccine can be done e.g. intradermally, subcutaneously, intramuscularly or intravenously. Apart from the immunogenic compound the vaccine also may contain stabilizers, adjuvants, solubilizers, buffers, etc.

The vaccine may contain additionally other immunogens, like antigens of parvovirus, swine influenza virus, TGE virus, rotavirus, *Escherichia coli*, atrophic rhinitis, Erysipelas.

The vaccine with the antibodies against the gII-derived polypeptide may be administered as a single dose, optionally in a slow release dosage form, or repeatedly. The route of administration for this vaccine is preferably by intradermal, subcutaneous, intramuscular or intravenous injection. This vaccine may contain also stabilizers, solubilizers, buffers, etc.

DESCRIPTION OF THE DRAWINGS

FIGS. 1.1–1.5 are a representation of the DNA sequence and a portion of the corresponding amino acid sequence of the Phylaxia strain of Pseudorabies Virus.

EXAMPLES

Procedures

1. Virus and cell culture

The virulent PRV strain PHYLAXIA was propagated and plaque-purified in Madin Darby bovine kidney cells (MDBK, ATCC CCL 221) or in SK-6 porcine kidney cells. The cells were maintained in Eagle minimal essential medium (MEM) with 10% newborn calf serum (Boehringer, Mannheim, FRG) and 100 units/ml penicillin and 100 µg/ml streptomycin. For growth of virus also BHK (baby hamster kidney) cells were used in Dulbecco modified minimal essential medium (DMEM). Virions were purified from the supernatant of infected cells (ca. 5 pfu/cell) by differential centrifugation and velocity sedimentation through 12 to 52% (w/v) sucrose gradient as recently described (Lukàcs et al., 1985). The virion band was aspirated, diluted with 0.2M Tris-HCl, 5 mM EDTA, 0.15M NaCl, and concentrated by pelleting in a SW27 rotor (Beckman) at 25.000 rpm, 4° C. for one hour.

2. Production of monoclonal antibodies

Monoclonal antibodies (Mab) against structural PRV proteins were produced as described (Lukàcs et al., 1985). In brief, the purified PRV virions were heat-inactivated at 60° C. for one hour and used for intraperitoneal immunization of BALB/c mice (50 µg protein in complete Freund adjuvant). After the last immunization the mouse spleen cells (ca. $3 \times 10^8$ cells) were fused with ca. $10^8$ Sp2/0-Ag14 myeloma cells by the use of polyethylenglycol (PEG). The cells were cultured on feeder cells (peritoneal mouse macrophages) in HAT medium containing 20% fetal calf serum (Boehringer, Mannheim, FRG) at 37° C. in a 5% $CO_2$ atmosphere. Hybridoma cell supernatant was tested for the production of PRV-specific antibodies in enzyme-linked immunoassay (ELISA). For that purpose, purified, sonicated PRV was coated onto 96 well plates (300 ng protein/well) and bound antibody was detected with peroxidase-labelled F(ab')$_2$ fragment of goat anti-mouse antibody (Tago Inc., Burlingame, USA). Positive hybridoma cultures were cloned and recloned by limiting dilution.

3. Determination of isotype

The immunoglobulin class of the individual Mab was determined by immunodiffusion. After ammonium-sulfate precipitation the hybridoma supernatants were tested with rabbit anti-mouse immunoglobulin sera (Nordic Immunol.) overnight at 4° C.

4. Radioimmuno precipitation

Infected cells (20 pfu/cell) were radiolabelled between 4 and 8 hours after infection (p.i.) either with [$^{35}$S]methionine (>1000 Ci/mM; Amersham Buchler, Braunschweig, FRG) or with D-[6-$^3$H]glucosamine (40 Ci/mM; Amersham Buchler, Braunschweig, FRG) as described (Lukàcs et al., 1985). Purified virions or infected cells were lysed in lysis buffer (phosphate-buffered saline containing 1% Nonidet P40, 0.1% deoxycholate, 0.1% sodium azide, 1 mM phenylmethylsulfonyl fluoride, 1 mM methionine and 2.5 mM potassium iodide). After centrifugation for 1 hour at 39.000 rpm in a Beckman 50 Tirotor, the lysates were preadsorbed with S. aureus and precipitated with hybridoma supernatants as described (Lukàcs et al., 1985). The washed immunoprecipitates were heated at 95° C. for 2 minutes in sample buffer (0.12M Tri-HCl pH 6.8, 4% SDS, 20% glycerol) in the presence or absence of 10% 2-mercaptoethanol and run in SDS-PAGE.

5. SDS polyacrylamide gel electrophoresis (SDS-PAGE)

The viral proteins were separated by SDS-PAGE in 7 or 10% polyacrylamide gels cross-linked with bisacrylamide as described earlier (Lukàcs et al., 1985).

6. Western blotting

Purified virion proteins were separated in SDS-PAGE, the gel renatured for 30 min. at room temperature in 50 mM NaCl, 10 mM Tris-HCl pH 7.0, 4M Urea and 0.1 mM dithiothreitol and transferred electrophoretically to nitrocellulose filter (Schleicher & Schüll, Dassel, FRG) in electrophoresis buffer without SDS for 2 hours at 30 V (1.0 A). After transfer the filter was incubated in PBS containing 3% bovine serum albumin (BSA) for 2 hours at room temperature and incubated overnight at room temperature with undiluted hybridoma supernatant. After washing the filter in PBS containing 0.1% Triton X-100 and in PBS with 1.0M NaCl, it was incubated with peroxidase-conjugated F(ab')$_2$ fragment of goat anti-mouse immunoglobulin G (Tago Inc., Burlingame, USA) and developed with chloronaphtol-H$_2$O$_2$ as described (Lukàcs et al., 1985).

7. Neutralization test

The in vitro neutralizing activity of the Mab was tested in the presence and in the absence of complement. Plaque-titrated virus was mixed together with ascites fluid of anti-gII Mab in a volume of 200 μl. As a source of complement 5% rabbit normal serum was used. The mixture was incubated at 37° C. for one hour followed by plaque titration on MDBK cells in 24 well plates (Costar). Serial dilutions of the reaction mixture (100 μl per well) were added to confluent monolayer cells and incubated for 1 hour at 37° C. After washing with PBS the cells were overlaid with semi-solid medium containing 1.5% methylcellulose. Plaques had developed after 3-4 days at 37° C. and the cells were fixed with 5% formaline before staining with crystal violet (1% in 50% ethanol).

8. Mice protection assays

Dilutions of Mab ascites fluid (1-3 mg IgG/ml) were made in MEM medium and 250 μl of them were injected intraperitoneally into C57/BL10 mice (6 weeks old). The animals were challenge infected 24 hours later with strain PHYLAXIA (22-27 TCID$_{50}$) and death was monitored during 10 to 14 days.

9. Grouping of anti-gII Mab

An indirect competition ELISA was performed for defining epitope specificity of anti-gII Mab. Hybridoma supernatant diluted with PBS containing 0.1% BSA was incubated overnight at 37° C. with clarified supernatant of PRV-infected cells. Thereafter, 200 μl of this mixture was incubated in microtiter plates coated with Mab ascites fluid (0.2 μg protein per well) for one hour at 37° C. After three washing steps with 0.05% Tween 20 in PBS goat PRV hyperimmune serum (1:500 diluted) was added and incubated for another hour at 37° C., washed before incubating with peroxidase-conjugated rabbit anti-goat IgG (Dianova). After one hour at 37° C. and washing of the plate the reaction was developed with 1,2-phenylene-diamine (Sigma), stopped with 2M sulfuric acid and the optical density at 420 nm was determined.

10. Selection of "mar"-mutants

Natural occurring mutants resistant to the neutralization of individual anti-gII Mab (designated as mar-mutants) were selected by passaging strain PHYLAXIA in BHK cells in the presence of Mab and complement. For that purpose PRV and ascites fluid of Mab sufficient for complete neutralization of the wild-type virus (1-10% ascites) was incubated for 1-2 hours at 37° C. and thereafter plaque-titrated. Surviving virus plaques were picked, again neutralized with Mab and tested in neutralization assay. Single plaques were further propagated in the presence of Mab and complement (5% rabbit normal serum) and this procedure was repeated at least three times until stable neutralization-escape mutant virus had been obtained.

11. Surface immunoassay

Monolayer cell cultures were infected with strain PHYLAXIA or with the different mar-mutants and a plaque assay was performed as described in 7. omitting the fixation step. After removing the methylcellulose and washing the cells with medium, Mab diluted with normal horse serum was added. All incubations were done at 37° C. unless otherwise indicated. After one hour the cells were washed and incubated with biotin-labelled anti-mouse IgG (Vectastain, ABC reagent) for another hour. Then the washed cells were incubated for 40 minutes with peroxidase-conjugated streptavidin-biotin complex (Vectastain, ABC reagent; diluted with PBS/0.1% BSA and preincubated for 30 minutes at room temperature), again washed and 4-chloro-1-naphtol/H$_2$O$_2$ used to detect the binding of Mab onto the surface of the infected cells (plaques).

12. DNA cloning

Purified PHYLAXIA DNA was cleaved with restriction endonucleases, and cloned into plasmids (pBR325, pUC19) according to standard procedures. Subcloning of viral DNA fragments in phage M13mp19 was achieved essentially as described (J. Messing, 1983, in: Methods Enzymol. Vol. 101, 20–78; ed. by R. Wu, L. Grossman & K. Moldave, Academic Press).

13. Marker rescue

Subconfluent BHK cells were co-transfected with total viral DNA (ca. 1.0 μg) and recombinant plasmid or double-stranded phage DNA (ca. 10 μg) according to the calcium phosphate precipitation method (Graham et al., 1973, Virology 52, 456–467). After the development of a cytopathogenic effect progeny virus was tested in in vitro neutralization and immunosurface assays.

14. DNA sequencing of the 'mar-epitopes'

The part of the gII-gene of the different mar-mutants predicted by marker rescue to contain the mutation, was sequenced and compared to wild-type PRV (strain PHYLAXIA) DNA-sequence. To this end, the purified DNA of the mutants m5/14, ml/5, mIN4, and mN4, respectively, was cleaved by restriction enzyme Sal I, the fragment 1A (METTENLEITER, T. C. ET AL., Virology 152, 66, 1986) was isolated from agarose gel and cloned into the bacterial plasmid pTZ19R (PHARMACIA). Three different cloned fragments 1A of each mutant DNA were used for doublestranded DNA sequencing using T7-DNA polymerase (TABOR, S. & C. C. RICHARDSON, Proc. Natl. Acad. Sci. USA 84, 4767, 1987). To sequence both strands of each plasmid 20mer primers flanking the predicted 'mar-epitope' (gII sequence position 1750–1769 and 2126–2145, respectively) were synthesized. In addition, fragment 1A of PHYLAXIA was also sequenced by the same strategy.

15. Cloning of gII fragments and preparation of fusion proteins

Expression plasmid pTSX-4.

An 1180 bp XhoI fragment (isolated from plasmid pASP411, containing gII DNA sequences) was cloned in SmaI-cleaved pBDI. After induction of pTSX-4-containing bacteria a β-gal gII fragment fusion protein with an apparent mol.wt. of 77 kD is synthesized by this expression system. Mass culture of pTSX-4 containing bacteria was grown in LB/Amp+0.5% glucose, IPTG-induction (0.5 mM), overnight at 37° C. Bacterial pellet was treated with lysozyme, NP40, DNAseI and ammonium sulphate precipitated. The lysate was separated in preparative SDS-PAGE and the fusion protein band cut out and electro-eluted with 1M NH₄HCO₃. Eluted material was lyophilized, suspended in PBS whereafter the concentration of fusion protein was determined according to Lowry (0.4 mg/ml) and tested for purity in SDS-PAGE/silver staining.

Expression plasmid pRZPS-3.

A 354 bp PstI fragment (isolated from plasmid pASP411, containing gII DNA sequences) was cloned in PstI-cleaved pUR291. After induction of pRZPS-3 containing bacteria a β-gal gII fragment fusion protein with an apparent mol.wt. of 125 kD is synthesized by this expression system.

The preparation of said fusion protein was achieved as described above (concentration: 0.95 mg/ml).

EXAMPLE 1

Characterization of Mab

1.1. gII specificity

Hybridoma supernatants producing PRV-specific antibodies (as determined by ELISA) were further analyzed by radioimmuno-precipitation and Western blotting to select for gII-specific Mab. This major envelope constituent of PRV represents a glycoprotein complex consisting of three glycoproteins gIIa, gIIb, and gIIc linked together via disulfide bonds which are demonstrable under reducing conditions (in the presence of e.g. 2-mercapto-ethanol). Under non-reducing conditions a single protein with an apparent molecular weight of ca. 155 kd can be detected. After Western blotting the reaction of the Mab with the different gII subunits can be demonstrated.

1.2. Grouping of the anti-gII Mab

For the evaluation of different antigenic sites recognized by the Mab a competitive ELISA was used. After reacting with a first Mab the PRV was tested for its ability to bind to another second Mab coated onto the test-plate. The results indicated that at least 4 topologically distinct domains exist on the gII (Table 1).

TABLE 1

Competitive ELISA for grouping different anti-gII Mab

| | Mab 2 | | | | | | |
|---|---|---|---|---|---|---|---|
| Mab 1 | 5/14 | N4 | N3 | IN4 | 1/5 | 2/22 | N12 |
| 5/14 | + | + | + | − | − | − | − |
| N4 | + | + | + | − | − | − | − |
| N3 | + | + | + | − | − | − | − |
| IN4 | + | + | + | + | + | − | − |
| 1/5 | ± | + | ± | ± | + | − | − |
| 2/22 | | | | | | + | |
| N12 | − | − | − | ± | ± | ± | + |
| Group: | | A | | B | C | D | E |

Legend:
Mab1 = coated onto plate
Mab2 = used for preincubation with virus
+ refers to inhibition of binding after Mab 2 had reacted with PRV
− refers to no inhibition
± indicates no unequivocal conclusion as to inhibition in the ELISA
blanks mean that no ELISA was done for that case.

1.3. Neutralizing activity

The ability of the anti-gII Mab to neutralize PRV in vitro was tested both with and without complement. It could be shown that all Mab were reactive in the presence of complement, and one Mab neutralized PRV also in the absence of complement (Table 2). Fractionated PRV hyperimmune serum with a high titer of neutralizing antibodies showed that the gII-specific fractions did also neutralize PRV in vitro.

TABLE 2

Properties of anti-gII Mab

| Mab | | Neutralization | | Protection | |
|---|---|---|---|---|---|
| # | Isotype | +C' | −C' | % protec. | died/total |
| 5/14 | IgG 1 | 4.4 | — | 25 | 15/20 |
| IN4 | IgG 2b | 5.1 | — | 5 | 19/20 |
| N4 | IgG 2a | 5.3 | — | 37½ | 5/8 |
| N3 | IgG 2b | 5.0 | — | 27 | 13/18 |
| 1/5 | IgG 2b | 5.3 | — | 35 | 13/20 |
| 2/22 | IgG 1 | 2.0 | — | 50 | 5/10 |
| N12 | IgG 1 | 3.4 | 2.7 | 84 | 3/19 |

Legend:
Neutralization test was performed in the presence of complement (+C'; 5% rabbit normal serum) or in the basence of complement (−C'). Titers are given as $-\log^{10}$ of antibody dilution showing 50% plaque reduction.

1.4. Protective activity

Passive immunization of mice with different anti-gII Mab conferred different degrees of protection against a lethal challenge infection with strain PHYLAXIA. The protection rate ranged between 5 to 85% of animals surviving challenge (Table 2).

Using combinations of some anti-gII Mab a synergistic effect could be observed in protection. Whereas the application of the single Mab conferred only partial protection of mice (see Table 1), the combined immunization increased the protection rate up to 70 to 100% of animals (Table 3).

TABLE 3

Protection of mice after passive immunization with combined application of anit-gII Mab.

| Mab # | Group | Protection | |
|---|---|---|---|
| | | % | (protected/total) |
| 5/14 | A | 100 | (10/10) |
| IN4 | B | | |
| 2/22 | D | | |
| 5/14 | A | 70 | (7/10) |
| 1/5 | C | | |
| N3 | A | 80 | (8/10) |
| N4 | A | | |
| 1/5 | C | | |

From the data described above it appears that antibodies against gII might play an important role in neutralizing PRV infectivity. Furthermore, this envelope protein is found to be expressed regularly and in similar amounts in numerous PRV strains and field isolates tested. Finally, the gII of PRV displays extensive homology to the glycoprotein gB of herpes simplex virus (Robbins et al., 1987) which is involved in natural killer cell recognition and cell-mediated immunity.

EXAMPLE 2

Characterization of the mar-mutants

The following mutants could be obtained after selection with the Mab 5/14 (m5/14), Mab 1/5 (m1/5$_{(1)}$ and m1/5$_{(2)}$), Mab IN4 (mIN4$_{(1)}$ and mIN4$_{(2)}$), and Mab N4 (mN4$_{(1)}$ and mN4$_{(2)}$).

In addition to their resistance in neutralization, the mutants also did not bind the homologous Mab in immunosurface binding assay. The mutants m1/5 and mIN4 were completely neutralized and recognized by the heterologous Mab. The mutant m5/14 was resistant in neutralization against the Mab N3 and N4, but neutralized by the other heterologous Mab. Analogous results were found for the mutant mN4 and the Mab 5/14 and N3. After testing both mutants in immunosurface binding assay the m5/14 virus did not react with the Mab N4, but bound the other heterologous Mab. In contrast, the mN4 virus displayed also binding of the Mab 5/14 (Table 4).

TABLE 4

| mAB | Cross Neutralization Test "mar"-Mutants | | | |
|---|---|---|---|---|
| | m5/14 | m1/5 | mIN4 | mN4 |
| 5/14 | − | + | + | − |
| IN4 | + | + | − | + |
| N4 | − | + | + | − |
| N3 | − | + | + | − |
| 1/5 | + | − | + | + |
| A4 | + | + | + | + |
| A15 | + | + | + | + |
| A25 | + | + | + | + |
| A33 | + | + | + | + |
| B3 | + | + | + | + |
| B16 | + | + | + | + |

TABLE 4-continued

| mAB | Cross Neutralization Test "mar"-Mutants | | | |
|---|---|---|---|---|
| | m5/14 | m1/5 | mIN4 | mN4 |
| B24 | + | + | + | + |

Legend:
+ neutralization
− no neutralization

These results indicate that 5/14 and N4 antibodies might be directed against two overlapping epitopes. Alternatively, the mutation in m5/14 might have led to a conformational alteration inhibiting binding of the Mab N4.

In conclusion, the existence of at least 4 different epitopic sites of neutralizing antibodies in gII was demonstrated, which is in accordance with the results of the competitive ELISA (1.2.). Domain A is recognized by the Mab 5/14, N4 and N3, domain B specific for Mab 1/5, C for Mab IN4 and at least one additional epitope recognized by the remaining neutralizing Mab.

The expression of gII in the mar-mutants was investigated by radioimmunoprecipitation tests. In principle, the same pattern of reactivity was found as already described for neutralization and immunosurface binding of the different anti-gII Mab. All mutants produced a gII protein qualitatively not altered as compared to wild-type PRV. It appears that the mutant mIN4 might synthesize reduced amounts of gII. No reaction was found after testing the mutant m5/14 and m1/5 with the Mab used for selection, whereas the homologous Mab precipitated only low amounts of gII of the two other mutants. The heterologous Mab precipitated gII of all mar-mutants, except of Mab 5/14 which was not able to precipitate the mutated gII from mN4 virus.

Thus, it can be concluded that the resistant phenotypes arose from mutations which either altered the conformation or the amino acid sequence of the epitopic sites of gII.

EXAMPLE 3

Identification of the 'mar-epitope'

Figure 2:
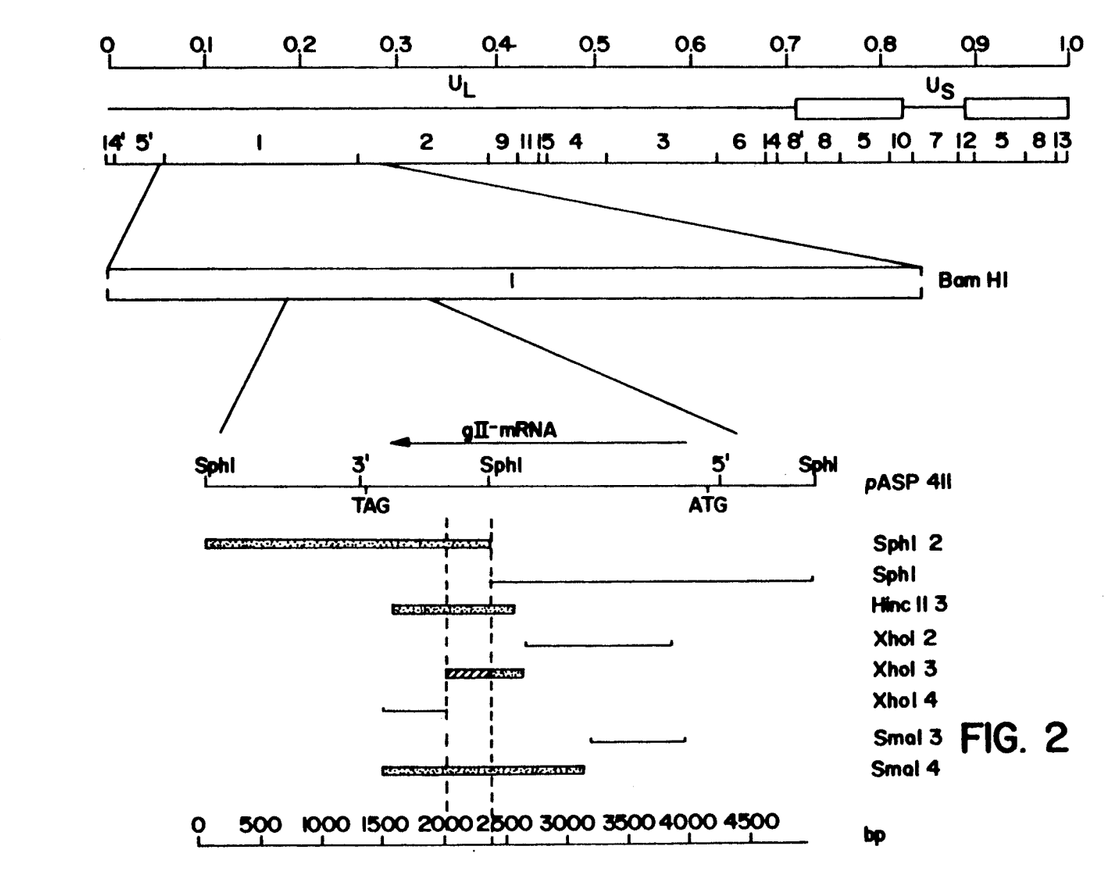
FIG. 2 is a depiction of the wild-type resistant PRV phenotype.

This was done using so-called 'marker rescue' experiments. In this assay cloned wild-type DNA fragments spanning the complete gII coding region were used to replace the corresponding parts in the mutant virus genome. After co-transfection of mutant virus DNA and cloned DNA fragment the progeny virus was tested in neutralization and immunosurface binding assay. As depicted in FIG. 2 the wild-type phenotype was rescueable with all mar-mutants after co-transfection with the complete gII gene (pASP411), with the SphI fragment 2, HincII fragment 3, XhoI fragment 3, and Sma fragment 4. After co-transfection of the mar genomes with the other DNA fragments (and also with control plasmids pBR325 and M13mp19) the resistant phenotype was retained. These results demonstrate that the epitopic sites of the neutralizing antibodies used for selection of the mutants are located in a region of 356 basepairs in size. The upper limits of this gII region are defined by the SphI fragment 2 (5' end) and the XhoI fragment 3 (3' end). The DNA sequence of strain PHYLAXIA (FIG. 1) reveals that this part of gII is quite hydrophilic and is predicted as a domain with high antigenic index. Furthermore, this region ends ca. 40 amino acids upstream of the putative transmembrane domain of gII.

EXAMPLE 4

DNA sequence of the different 'mar-epitopes'

Figure 3:
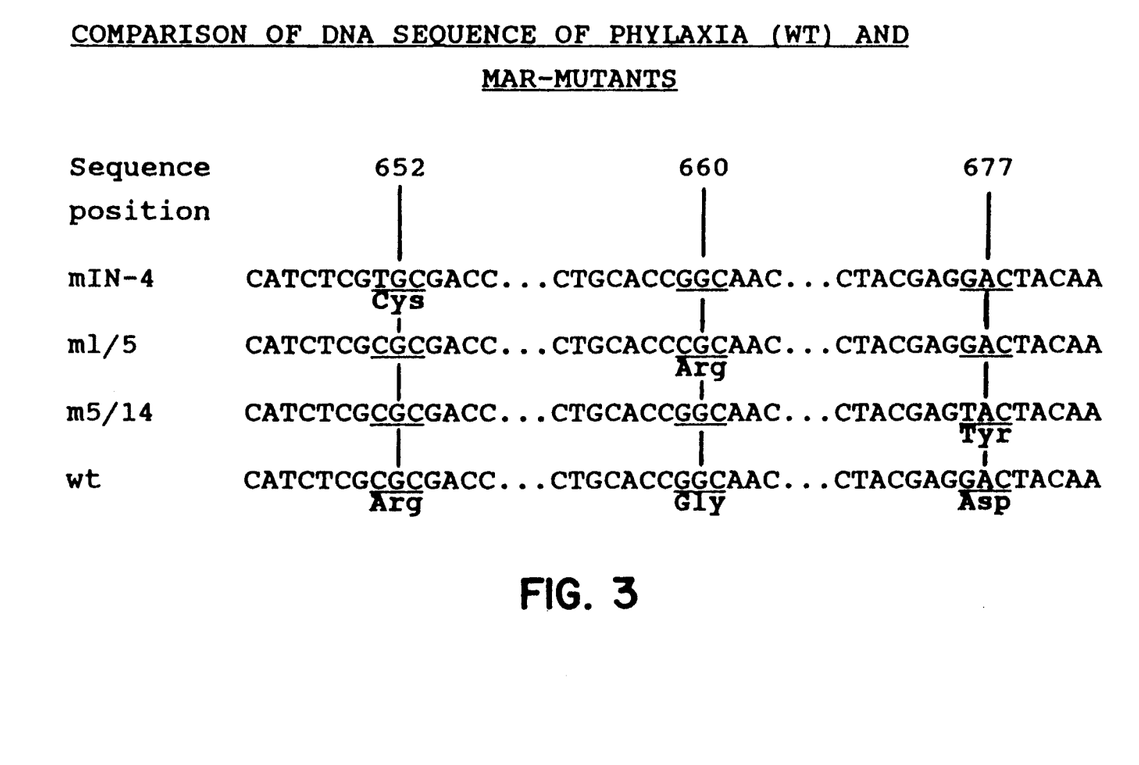
FIG. 3 is a comparison of the DNA sequence of the wild-type and mar-mutant Phylaxia strains.
Figure 11:
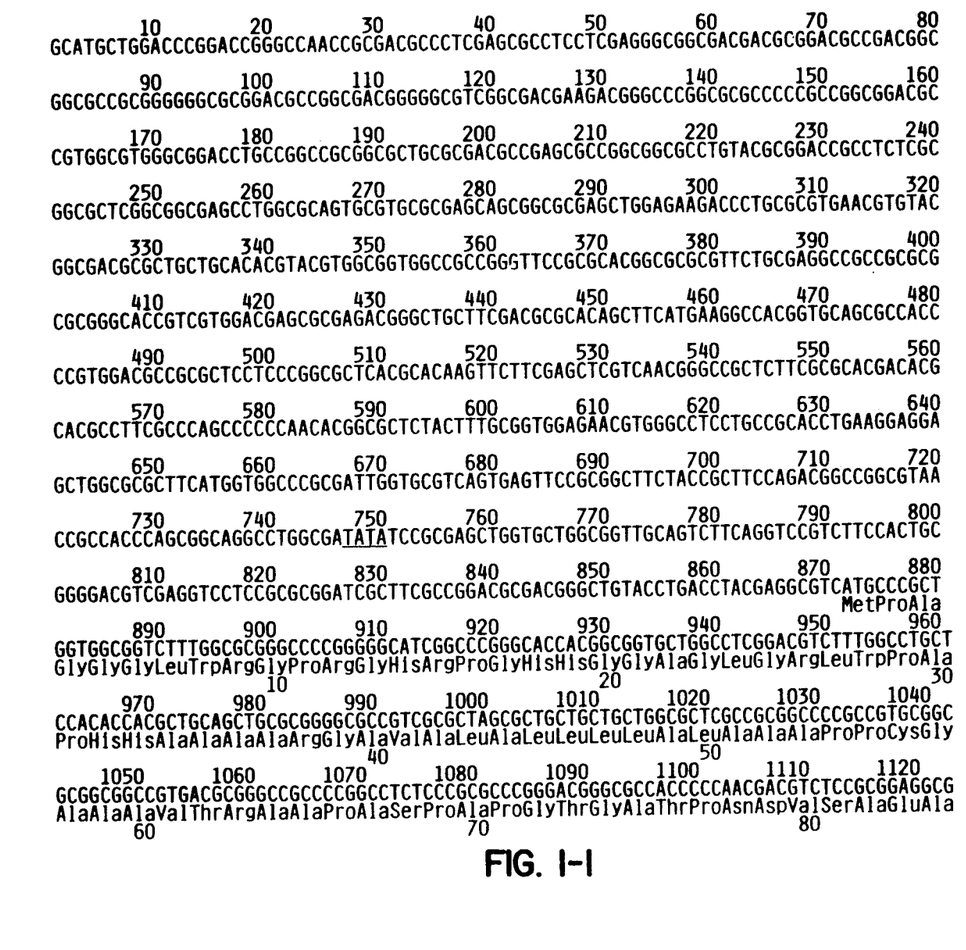
Figure 12:
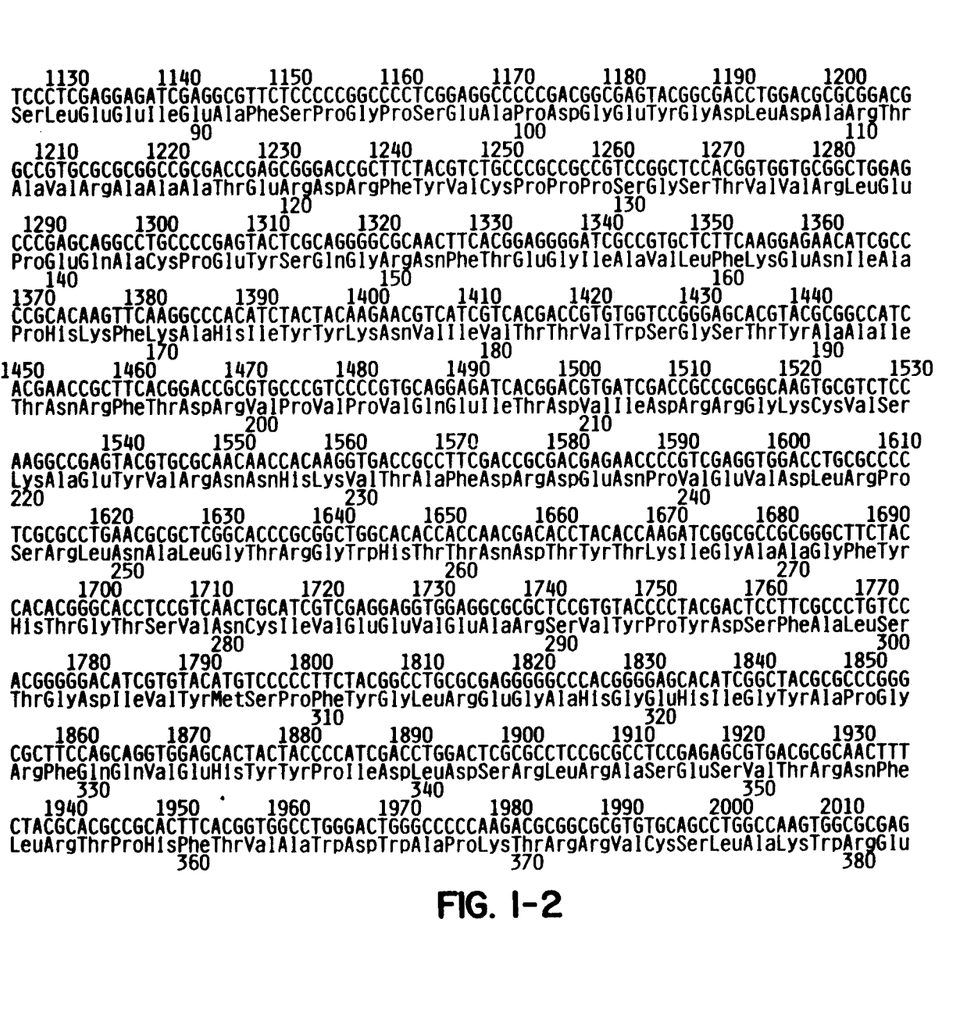
Figure 13:
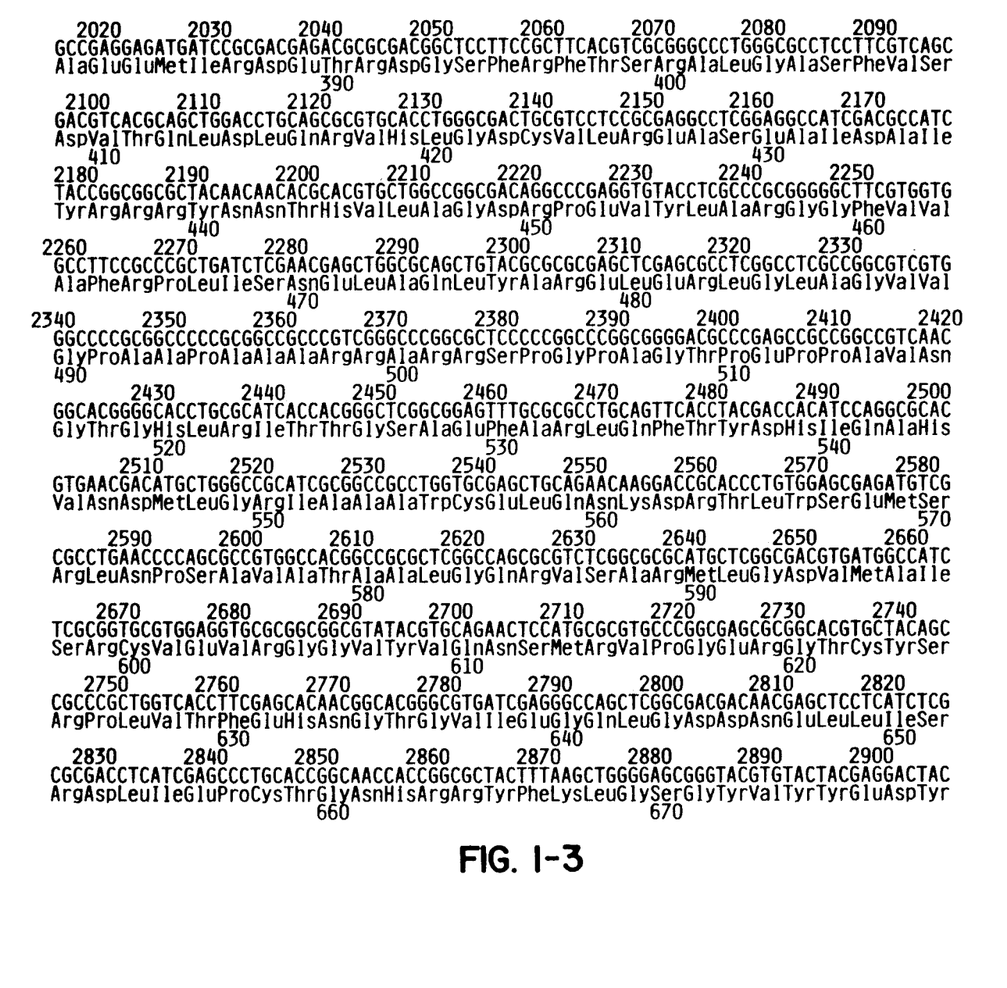
Figure 14:
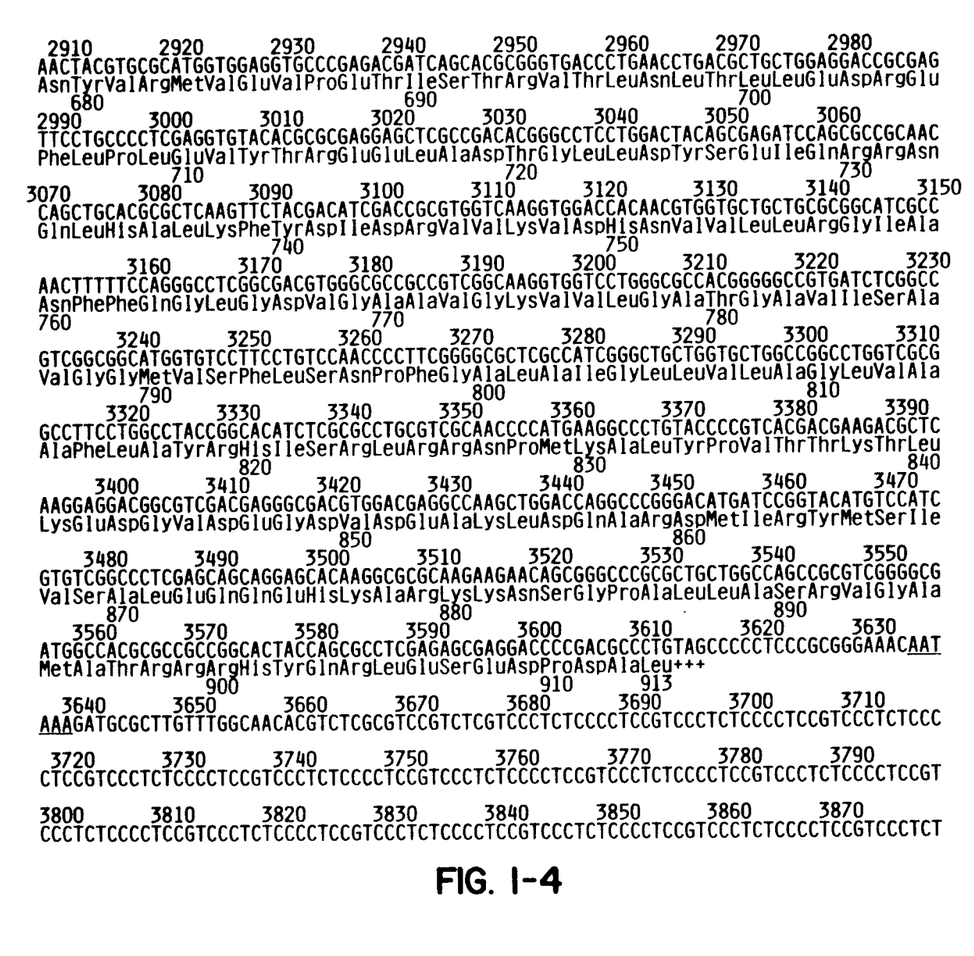
Figure 15:
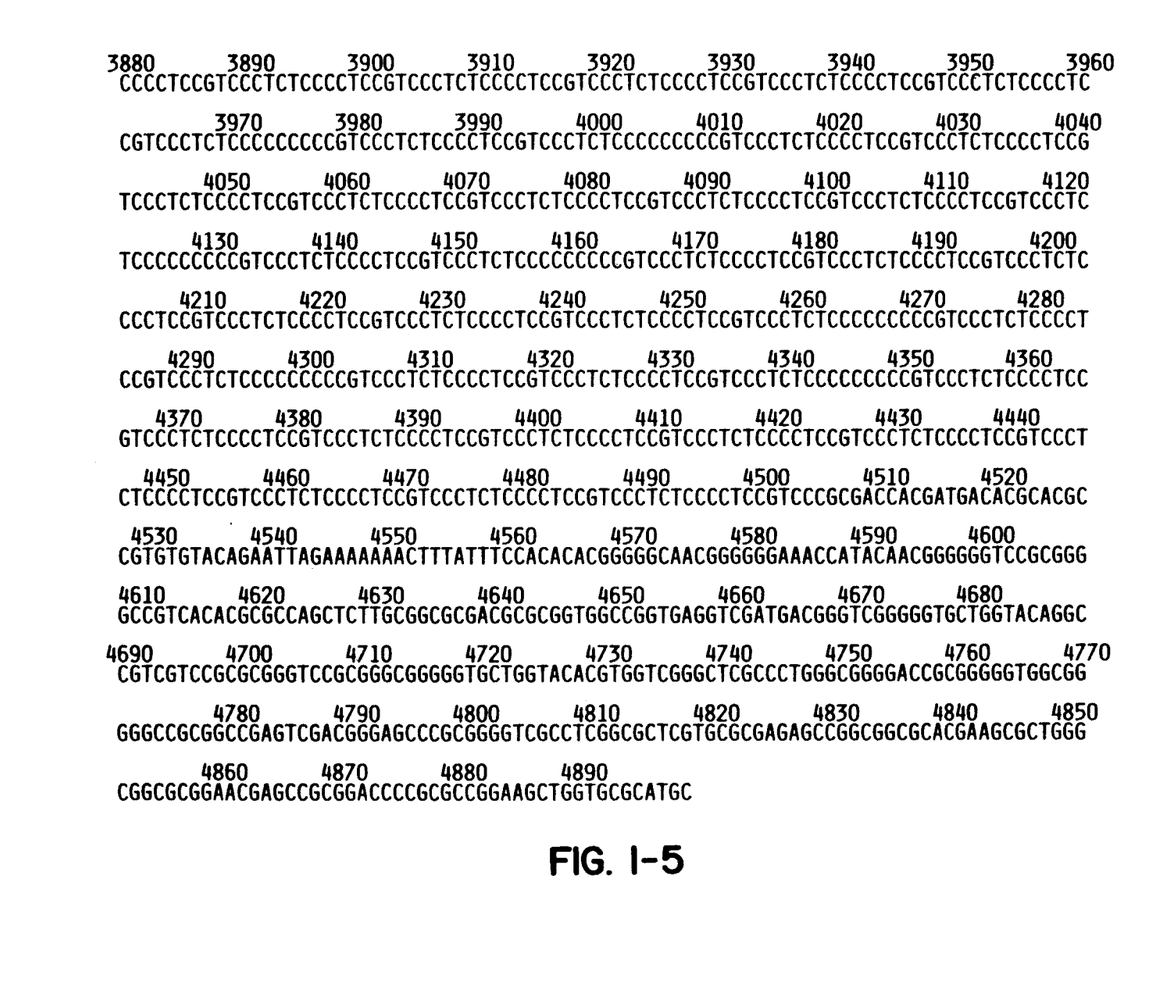

The DNA sequence of the mar-mutants m5/14, m1/5, and mIN-4 (both strands between position 1797 and 2103 were sequenced) was found to be altered in single bases differing from each other (FIG. 3), the mutant mN-4 exhibited the identical point mutation as m5/14. Sequencing of three different cloned fragments 1A of each mutant DNA showed identical results, thus the demonstrated single base exchanges do not represent cloning artefacts. The mutation affected always the first base of a codon leading to the amino acid exchange as depicted in FIG. 3.

Comparison of the predicted peptide structure of wt-gII and gII of the three mar-mutants revealed the loss of highly antigenic parts, which are exactly located around positions 652, 660 and 677, respectively. These alterations in the gII-genes of the mar-mutants explain the loss of binding of monoclonal antibodies resulting in the inability to neutralize the mutant virus.

EXAMPLE 5

Antibody response of gII fragment fusion proteins

The fusion proteins expressed by pRZPS-3 and pTSX-4 were purified by β-Galactosidase affinity chromatography according to the instructions of the manufacturer (Pharmacia).

The purified fusion proteins were emulsified in mineral oil using Tween 80 and Span 80 as emulsifiers.

With each fusion protein two rabbits were injected at different sides and boostered twice at 6-weeks interval. The sera obtained were tested in the Elisa and in the virus neutralisation (VN) test. After one injection antibodies reacting in the Elisa were found for both fusion proteins. However, after two booster injections neutralising antibodies were only found for the fusion protein resulting from pRZPS-3 (Table 5, rabbit no. 3869 and 3870).

TABLE 5

| Rabbit No. | fusion protein | Antibody response of fusion proteins | | | |
|---|---|---|---|---|---|
| | | Antibody titer | | | |
| | | Elisa | | VN | |
| | | 0 | 6 weeks | 0 | 22 weeks |
| 3869 | pRZPS-3 | — | 2 | — | 2 |
| 3870 | pRZPS-3 | — | 8 | — | 8 |
| 3871 | pTSX-4 | — | 128 | — | — |
| 3872 | pTSX-4 | — | 64 | — | — |

Those results demonstrate that neutralizing sites are located in a gII fragment encoded by a 354 bp PstI fragment of the gII gene.

We claim:

1. Purified polypeptide having an immunizing activity characteristic of glycoprotein gII of pseudorabies virus, consisting essentially of a fragment of a glycoprotein gII subunit protein said fragment corresponding to the amino acid sequence positioned between about amino acid no. 590 and 710 of said gII or subsequences thereof consisting of at least one epitope that reacts with virus neutralizing antibodies, substantially free of other envelope glycoprotein fragments.

2. Polypeptide according to claim 1, wherein the polypeptide is recognized by an antibody selected from the group consisting of 1/5, IN4 and N4.

3. Polypeptide according to claim 2, wherein the antibody is 1/5.

4. Polypeptide according to claim 2, wherein the antibody is IN4.

5. Polypeptide according to claim 2, wherein the antibody is N4.